United States Patent [19]

Chen et al.

[11] Patent Number: 5,080,667

[45] Date of Patent: Jan. 14, 1992

[54] STERILE SURGICAL NEEDLE-SUTURE COMBINATION

[75] Inventors: Chao Chen, Edison; Arthur Taylor, Plainfield, both of N.J.

[73] Assignee: Ethicon, Inc., Somerville, N.J.

[21] Appl. No.: 587,201

[22] Filed: Dec. 5, 1990

Related U.S. Application Data

[62] Division of Ser. No. 434,399, Nov. 13, 1989, Pat. No. 5,007,922.

[51] Int. Cl.⁵ .............................................. A61B 17/01
[52] U.S. Cl. .................................... 606/227; 606/225
[58] Field of Search ................................. 606/224-228

[56] References Cited

U.S. PATENT DOCUMENTS

| | | | |
|---|---|---|---|
| 295,612 | 3/1884 | Bailey | 606/224 |
| 1,665,216 | 4/1928 | Morton et al. | 606/224 |
| 3,799,169 | 3/1974 | Beroff et al. | 606/224 |
| 3,981,307 | 9/1976 | Borysko | 606/224 |
| 4,932,962 | 6/1990 | Yoon et al. | 606/224 |

Primary Examiner—Stephen C. Pellegrino
Assistant Examiner—Gary Jackson

[57] ABSTRACT

A needle-suture combination with reduced diameter portion of the suture being attached to the blunt end of the needle. The maximum diameter of the suture being almost the same but no larger than the diameter of the blunt end of the needle and the reduced diameter portion of the suture having a tensile strength greater than the remainder of the suture.

5 Claims, 4 Drawing Sheets

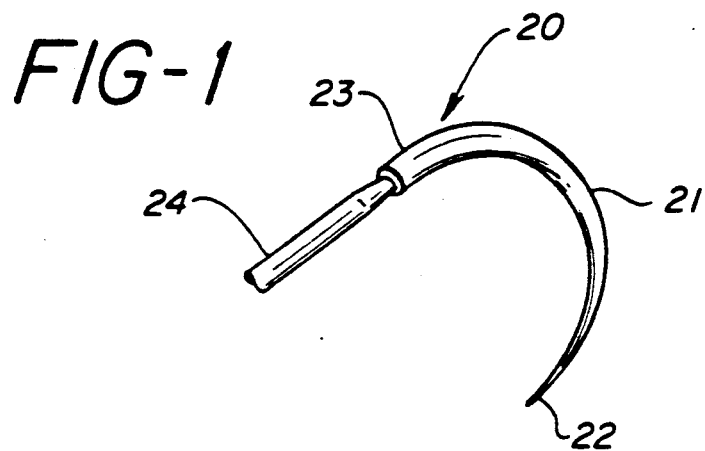
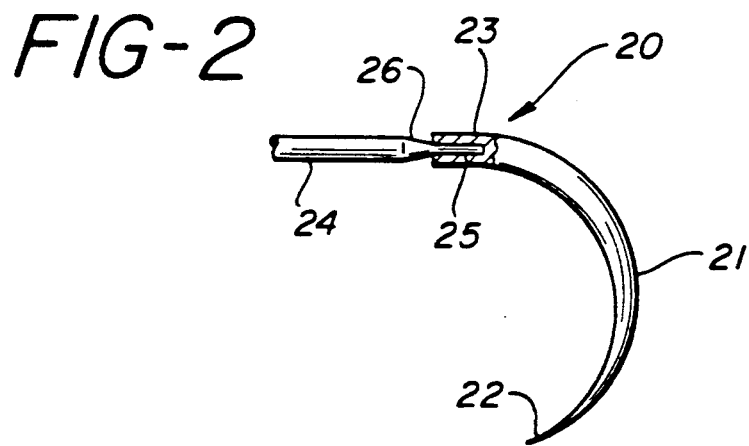
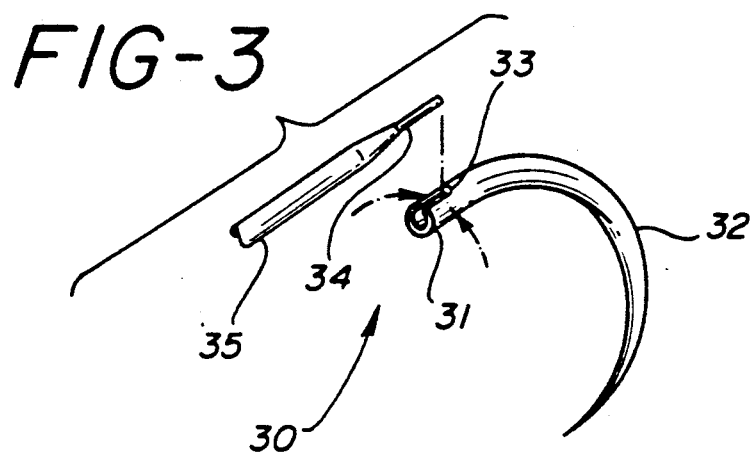

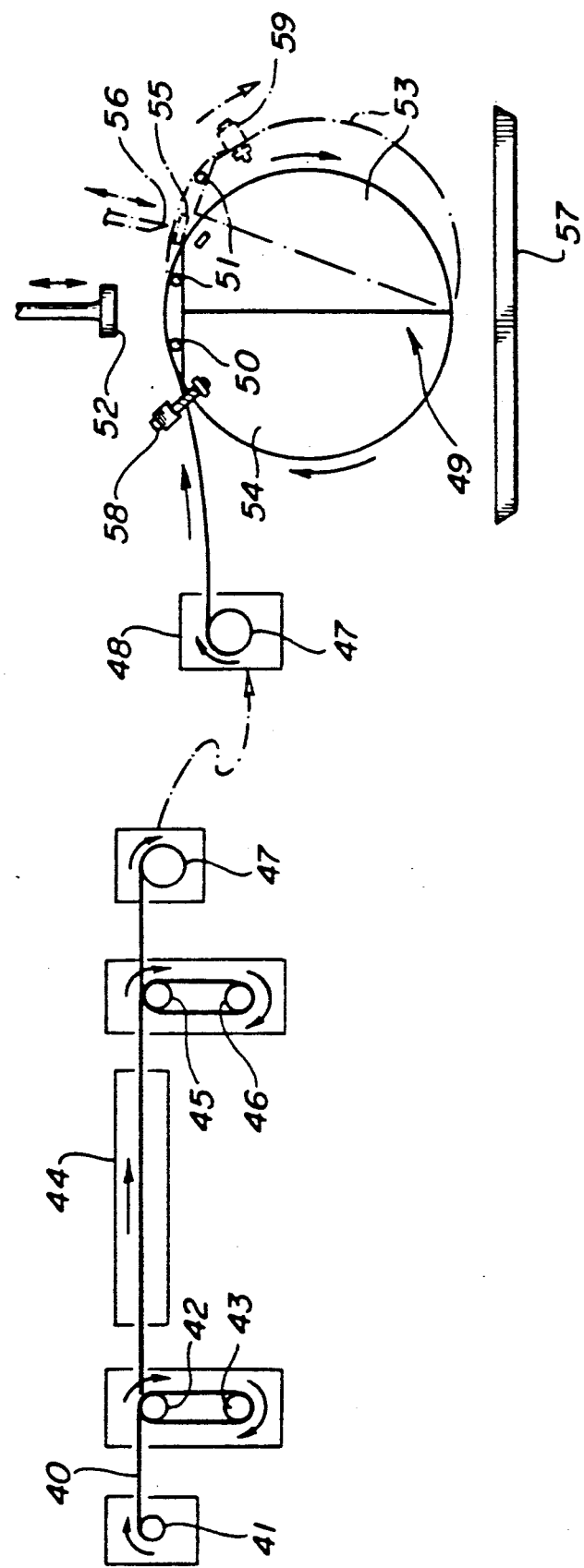

STERILE SURGICAL NEEDLE-SUTURE COMBINATION

This is a division of application Ser. No. 434,399, filed Nov. 13, 1989, now U.S. Pat. No. 5,007,922.

BACKGROUND OF THE INVENTION

In many surgical procedures, it is desirable that when joining tissue using surgical needles and sutures, that the maximum diameter of the needle; that is, the diameter at the blunt end of the needle, and the maximum diameter of the suture be as close to the same size as possible. This design is necessary so that the hole in the tissue produced by passing the needle through the tissue is substantially filled by the suture. This is especially important when joining vascular tissue to prevent oozing or seepage of blood through the hole produced by the needle.

Originally, surgical needles had an eye at the blunt end through which the suture was attached. As can be appreciated, this meant that the blunt end of the needle had sufficient size to allow for an eye to be placed in and that at least double the maximum diameter of the suture would be placed through that eye so that the hole produced when the needle was passed through tissue was substantially greater than the diameter of the suture. Over the years, to improve surgical procedures, various techniques have been developed to eliminate the eye in the blunt end of the needle and find other techniques by which the suture can be attached to the blunt end of the needle. Some of the techniques that have been developed are to place a channel in the blunt end and crimp the suture in that channel or swage the suture into a hole drilled in the blunt end of the needle. As can be appreciated, it is still required that the diameter of the blunt end of the needle be substantially larger than the diameter of the body of the suture and hence when such a needle-suture combination is used to join tissue, the suture still does not completely fill the hole formed by the needle.

In recent years, various techniques have been developed to reduce the diameter of the suture at the end that is to be attached to the blunt end of the needle and in many instances this has been accomplished so that the diameter of the body of the suture is substantially the same as the diameter of the blunt end of the needle. Some of these techniques are more fully described in U.S. Pat. No(s). 3,890,975 and 3,926,194. Though these techniques produce a needle-suture combination wherein the maximum diameter of the suture is close to the diameter of the blunt end of the needle, in order to accomplish this they all greatly reduce the strength of the suture in that area of the suture that is attached to the needle or immediately adjacent that area. This, of course, produces a weakened needle-suture combination. This problem restricts the various sizes of sutures that can be produced by these techniques especially the extremely fine size sutures. It also limits the types of materials that can be used to produce the sutures in that you must greatly increase the overall strength of the suture to have sufficient strength at the reduced diameter portion.

SUMMARY OF THE PRESENT INVENTION

It is an object of the present invention to produce a needle-suture combination, which when used to join tissue, the hole produced by the needle is substantially filled by the suture joining the tissue. It is a further object of the present invention to produce a needle-suture combination in which the area of the suture joined to the needle and the area adjacent that area has a tensile strength substantially greater than the remainder of the suture. It is a further object of the present invention to produce preferred needle-suture combinations wherein the diameter of the body of the suture is almost the same as the diameter of the blunt end of the needle. It is yet a further object of the present invention to be able to attain these desirable characteristics with all suture sizes especially the smaller size sutures.

The surgical needle-suture combination of the present invention comprises a surgical needle having a blunt end and a sharp point. A surgical suture has one end of the suture attached to the blunt end of the surgical needle. The diameter of the blunt end of the needle is somewhat larger or substantially the same as the maximum diameter of the suture or the diameter of the body of the suture. The portion of the suture attached to the blunt end of the needle and usually the portion immediately adjacent such attached portion has a reduced diameter as compared to t he diameter of the body of the suture. In the preferred embodiments of the surgical needle-suture combinations of the present invention, the reduced diameter portion has a tensile strength at least 50% greater than the tensile strength of the body of the suture.

The present invention also includes the method for producing a surgical suture having a reduced diameter portion from monofilaments of various polymeric materials. The monofilament is helically wound to form a cylinder comprising a multiplicity of convolutions of the monofilament. Adjacent portions of each convolution are heated to an elevated temperature and the heated portions are then drawn to increase the length of the heated portions while reducing the diameter of the heated Portions. This heating and drawing also increases the density and crystallinity of the heated and drawn portion. Each convolution is severed to form a suture having a reduced diameter end portion. Preferably, each convolution is severed approximately in the center of the reduced diameter Portion to form a suture having both ends of a reduced diameter.

DESCRIPTION OF THE DRAWINGS

FIG. 1 is a perspective view of a sterile surgical needle-suture combination of the present invention.

FIG. 2 is a cross-sectional view of the needle-suture combination of FIG. 1.

FIG. 3 is a perspective view of another embodiment of the sterile surgical needle-suture combination of the present invention.

FIG. 4 is a diagrammatic view of various steps in the process for producing needle-suture combinations

DETAILED DESCRIPTION OF THE INVENTION

Figure 5:
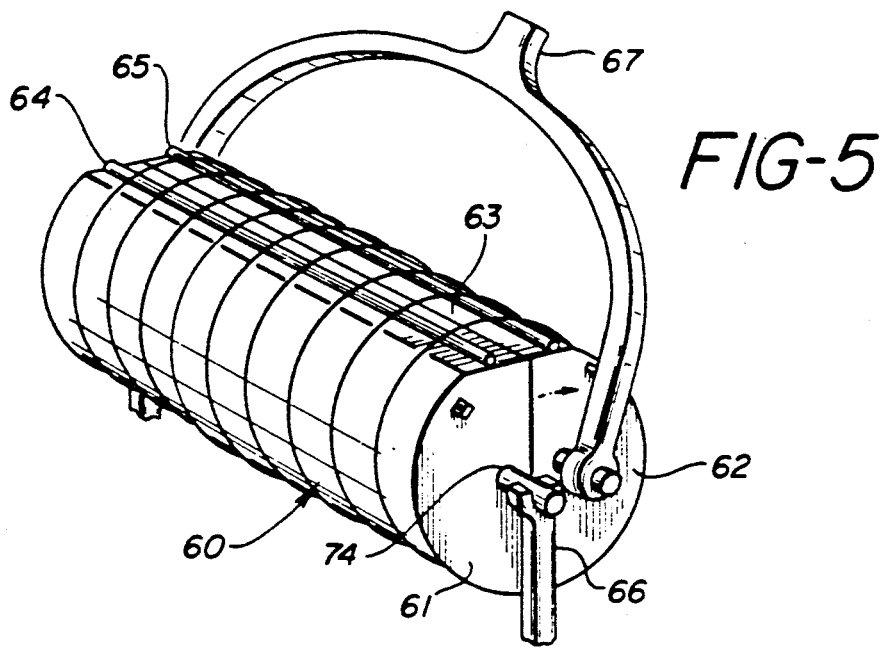
FIG. 5 is a perspective view of the stretching drum used in the present invention.

Referring to the drawings, in FIG. 1 there is shown one embodiment of this sterile surgical needle-suture combination 20 of the present invention. The needle 21 has a sharp end 22 or point and a blunt end 23 Attached to the blunt end is a surgical suture 24. As more clearly shown in the cross-sectional view in FIG. 2, the blunt end 23 has a hole 25 drilled into the center of the blunt end. The suture has a reduced diameter portion 26 which is inserted into that hole and attached to the blunt end of the needle. As may be seen in FIG. 2, the maximum diameter of the suture or the diameter of the body of the suture, is substantially the same as the maximum diameter of the needle or the blunt end of the needle.

In FIG. 3, there is shown another embodiment of the sterile surgical-needle suture combination 30 of the present invention. In this embodiment, the blunt end 31 of the needle 32 has a channel 33. The reduced diameter portion 34 of the suture 35 is placed in that channel and the channel crimped about the reduced portion of the suture to attach the suture to the needle.

The sutures used to produce the needle-suture combinations of the present invention may be any of the monofilament sutures such as polyethylene, polypropylene, polyester, nylon, polyglycolides, polyfluoro carbons, etc. The needles used in producing the needle-suture combinations of the present invention may be made from various metals such as stainless steel. The suture may be attached to the needle by any of the various techniques which allow for attachment of the suture to the blunt end of the needle, such as drilling a hole in the blunt end of the needle and adhering or attaching the suture into that hole either using adhesive or by crimping or by placing the suture in a channel and adhering it in the channel by crimping and/or adhesion or by various other techniques well known in the art.

Referring to FIG. 4, there is shown diagrammatically one method for producing surgical sutures which may be used in producing the surgical needle-suture combinations of the present invention. Extruded monofilaments 40 are supplied from a supply roll 41 and passed around a pair of rolls 42 and 43 called a "Godet" and the extruded monofilament then passed through a hot oven 44. The monofilament is then taken up on a second pair of rolls 45 and 46 or second "Godet" and then wound up on a wind up roll 47. The second pair of drawing rolls 45 and 46 are operated at a speed 16 slower than the first pair of drawing rolls 42 and 43, so that as the extruded monofilament passes through the oven the monofilament is relaxed. Depending upon the composition of the monofilament, the oven will be heated to a suitable temperature to allow the monofilament to relax. If a polypropylene monofilament suture is being produced, the oven would be maintained at about 285° F. The wound up relaxed monofilament on the wind-up roll 47 is moved to another feed station 48 and wound on a split drum 49. The diameter of the drum is such as to allow for the Production of the desired length of sutures. A portion of the surface of the drum has been flattened and there are a pair of bars 50 and 51 or rollers at the edges of this flattened surface so that when the monofilament is helically wound around the circumference of the drum, the portion of the monofilament extending between these two bars is displaced from the surface of the drum. The filaments are held in position by clamps 58 and 59 placed on the outside of the flattened section adjacent the rollers. A heater bar 52 is placed adjacent the portion of the monofilament which passes between these two bars and the monofilament warmed or heated. If the monofilament is made from polypropylene, it is heated by this heating bar to about 300° F. for from about 3 to 5 minutes. One section 53 or half of the drum is then displaced from the stationery half 54 of the drum to increase the circumference of the drum and draw or stretch the portion of the monofilament extending between the roller bars. The distance the filament is drawn of stretched will depend on the size of the suture being produced but may vary from two inches to three inches or more. Upon drawing, the diameter of the filament is reduced in the area that is drawn, that is, the area between the bars. After drawing, a cutting board 55 may be placed underneath the drawn portion and the drawn portion of the wound monofilament cut with a razor knife 56 substantially in the center of the drawn or stretched area. The cut sutures having reduced diameter portions at each end are dropped onto a tray 57. The tray is taken to another station where needles are attached to each end by swaging or other known techniques. The double-armed sutures are then wound and packaged as is well known. The needle-suture combination may then be sterilized by any of the techniques known in the art such as ethylene oxide, radiation, etc.

It is important that the drawing or stretching drum be circular or substantially circular in configuration to minimize any set or kink developing in the monofilament as a result of the processing.

Figure 6:
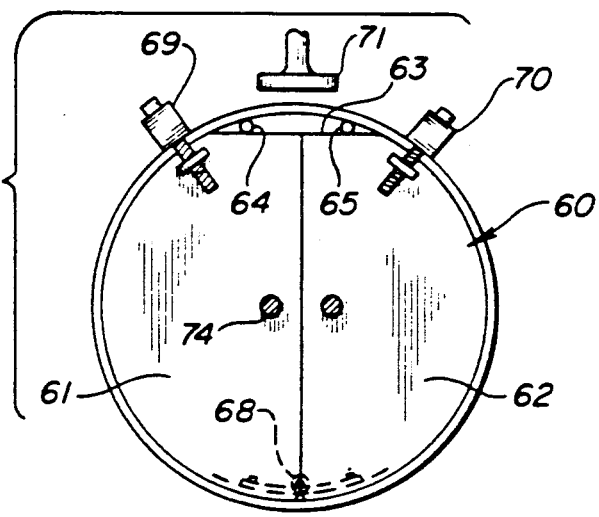
FIG. 6 is an end view of the stretching drum in its closed or initial original position.
Figure 7:
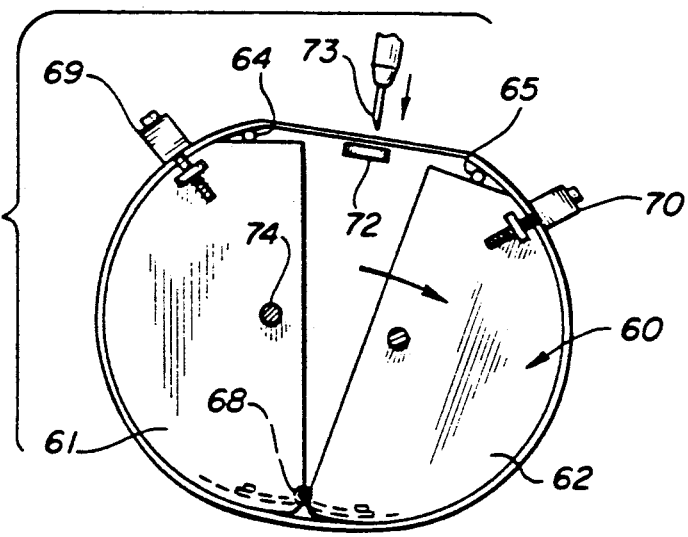
FIG. 7 is an end view of the stretching drum of FIG. 6 in its open position.
Figure 8:
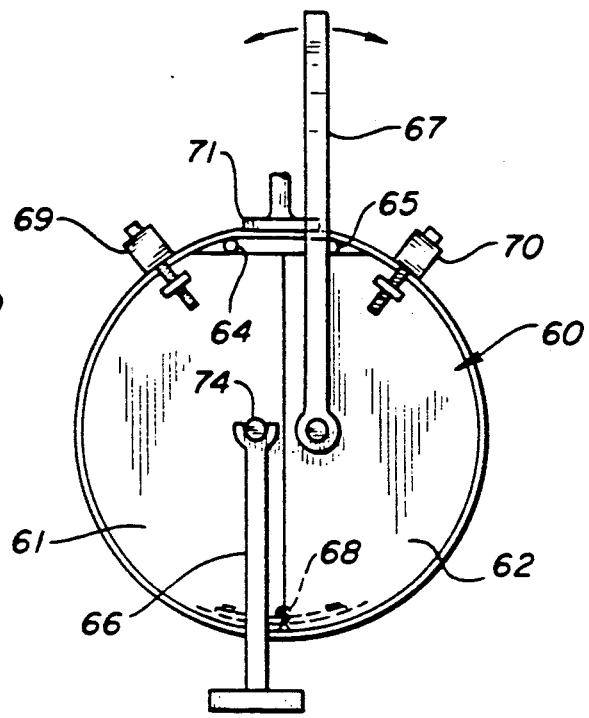
FIG. 8 is an end view of the stretching mechanism of FIGS. 6 or 7 which also shows mechanisms for moving the drum from the position shown in FIG. 6 to the position shown in FIG. 7.
Figure 9:
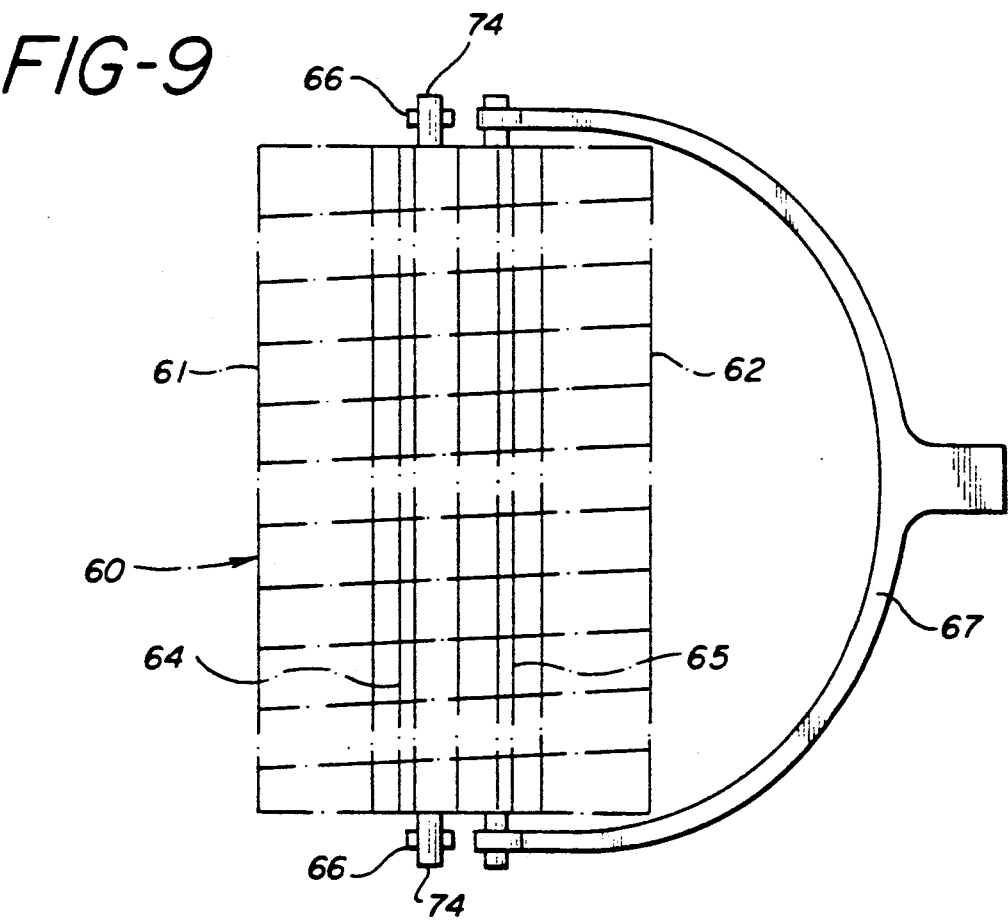
FIG. 9 is a top view of the mechanism shown in FIG. 8.

The stretching drum will be more fully described in conjunction with FIGS. 5 through 9. The drum 60 comprises two halves 61 and 62. Preferably, the drum is split slightly off-center so that the stationery half 61 is slightly larger than the moveable half 62. This configuration will allow the shaft 74 to be placed at the center of the closed drum. When the halves are adjacent, the drum has a substantially circular cross-section. The split drum is flattened for about 4 inches at the area 63 where one of the halves meets the other half of the drum. Disposed in this flat area about 4 inches apart are a pair of roller bars 64 and 65. One half of the drum is stationery and is attached to a stationery stand 66. The opposite half of the drum is moveable and is attached through a moveable yoke mechanism 67. The extruded monofilament is wound about the circumference of the drum. The length of the drum will determine the number of strands that can be made around the drum, and the diameter of the drum will determine the length of the sutures to be produced.

Opposite the flat section of the drum, the drums are attached by a hinge 68.

Once the sutures are wound about the drum, immediately adjacent each side of the flattened portion there are clamps 69 and 70 which are used to clamp the extruded monofilament winds to the surface of the drum. A moveable heater bar 71 is placed adjacent the monofilament winds at the flattened area of the drum to heat these positions of the winds to the desired temperature.

Once this portion has been heated sufficiently, the moveable yoke is moved away so as to displace the moveable half of the drum from the stationery half of the drum with the gap at its widest portion being from about two to four inches. This stretches each monofilament wind in the portion of the wind between the roller bars. A cutting surface 72 is placed under the stretched portion of the winds of the monofilament and a suitable razor knife 73 is passed along this cutting board to cut the monofilaments in the stretched areas and produce a plurality of sutures having a reduced diameter portion at each end of the suture. The sutures are collected, needles attached and packaged as is well known in the art.

The stretching of the monofilament material at the desired temperature produces a reduced diameter portion which portion has a tensile strength substantially greater than the remainder of the suture. The tensile strength may be as much as 50% to 60% greater than the tensile strength of the body of the suture.

The following is specific example for producing needle-suture combinations according to the present invention.

EXAMPLE

An extruded monofilament of polypropylene is produce and wound on a wind-up roll. The propylene monofilament is fed to first "Godet". The first "Godet" is operated at a speed of approximately 70 feet per minute and the monofilament is wrapped about this "Godet" approximately six times. The filament is passed through a hot air oven with the oven maintained at a temperature of about 285° F. The filament is wound on a second "Godet" with the second "Godet" being operated at a speed of approximately 60 feet per minute, so that as the monofilament passes through the oven it is relaxed about 16%. The relaxed monofilament is taken from the second "Godet" and wound up on a suitable wind-up roll.

The relaxed polypropylene monofilament is then wound on a split drum as described in conjunctions with FIGS. 5-9. The drum is about twelve inches in diameter and about 300 winds of the relaxed polypropylene monofilament cover the surface of the drum. An electric heater bar is placed against the portion of the monofilaments that pass between the two bars forming a portion of the surface of the drum. The polypropylene is heated to approximately 300° F. for about 5 minutes. The moveable section of the drum is then displaced from the stationery section of the drum to draw the heated portion of the monofilaments about 3 inches, to reduce the diameter of the monofilament in the Portion that passes between the two bars. A cutting surface is placed beneath the stretched portions of the monofilaments and a razor knife passed down the center of the stretched portions to cut the winds on the drum and form separate sutures which have a reduced diameter portion at each end. The cut sutures are collected and a needle having a channel in the blunt end is attached to each reduced diameter end of the suture to produce a double-armed suture. The sutures are suitably wound and packaged and sterilized using cobalt radiation. Size 3/0. 4/0 and 5/0 polypropylene sutures are produced as described above. The diameter, density (which is an indication of crystallinity) and the tensile strength of both the body portion and the reduced diameter portion of each of the sutures is measured. The 3/0 suture has a diameter in the body portion of 9.85 mils, a density of 0.9085 gm/cc$^3$ and a tensile strength of 67,000 lbs. per square inch while the reduced diameter portion of the size 3/0 suture has a diameter of 7.1 mils, a density of 0.9113 gm/cc$^3$ and a tensile strength of 109,000 lbs. per square inch. The diameter of the body portion of the 4/0 suture is 7.6 mils, a density of 0.9085 gm/cc$^3$ and the tensile strength 73,000 lbs. per square inch while the reduced diameter portion has a diameter of 5.2 mils, a density of 0.9112 gk/cc$^3$ and a tensile strength of 138,000 lbs. per square inch. The 5/0 suture has a diameter in the body portion of 5.7 mils, a density of 019103 gm/cc$^3$ and a tensile strength in this portion of 75,000 lbs. per square inch while the reduced diameter portion of the 5/0 suture has a diameter of 4.0 mils, a density of 0.9112 gm/cc$^3$ and a tensile strength of 129,000 lbs. per square inch.

The ratio of the diameter of the blunt end of the needle to the body diameter of the 3/0 suture is 1.46 to 1 as compared to a ratio of 2.08 to 1 for conventional 3/0 needle-suture combinations. The ratio of the diameter of the blunt end of the needle to the body diameter of the 4/0 suture is 1.51 to 1 as compared to a ratio of 2.24 to 1 for a conventional 4/0 needle-suture. The ratio of the diameter of the blunt end of the needle to the body diameter of a 5/0 suture is 1.62 to 1 as compared to a ratio of 2.16 to 1 for a 5/0 needle-suture.

Test methods used for determining the physical properties of monofilament suture materials were as follows:

Tensile strength is determined by A.S.T.M. method D-2256-66T at a constant rate of extension using an INSTRON table Model 4200 universal testing instrument manufactured by the Instron Corporation of Canton, Massachusetts. With the instrument sample clamps set 5 inches apart, 5-inch lengths of suture were elongated at a rate of 12 inches per minute until fracture.

The INSTRON instrument was set for the correct suture diameter, and Young's Modulus was calculated in psi from the initial stress-strain data generated during the straight tensile strength test. Young's Modulus is the ratio of applied stress to strain in the elastic region of the suture and measures the elastic component of a suture's resistance to stress. This value is related to the flexibility of a suture.

As many apparently widely different embodiments of this invention may be made without departing from the spirit and scope thereof, it is to be understood that the invention is not limited to the specific embodiments thereof except as defined in the following claims.

What is claimed is:

1. A sterile surgical needle suture combination comprising a surgical needle having a blunt end and a sharp point and a suture, one end of which is attached to the blunt end of the surgical needle, the diameter of the blunt end of the needle being slightly larger or substantially the same as the maximum diameter of the suture, the portion of the suture attached to the blunt end of the needle having a reduced diameter as compared to the maximum diameter of said suture and said reduced diameter portion of said suture having a tensile strength greater than the remainder of the suture.

2. A sterile surgical needle-suture combination according to claim 1 wherein the tensile strength of the reduced diameter portion of the suture is at least 50% greater than the tensile strength of the remainder of the suture.

3. A sterile surgical needle-suture combination according to claim 1 wherein the suture is polypropylene.

4. A sterile surgical-needle suture combination according to claim 1 wherein the blunt end of the needle includes a channel and the reduced diameter portion of the suture is attached to the channel.

5. A needle-suture combination of claim 1 wherein the blunt end of the needle includes a drilled hole and the reduced diameter portion of the suture is attached in the hole at the blunt end.

* * * * *